(12) United States Patent
Gesler et al.

(10) Patent No.: US 12,337,089 B2
(45) Date of Patent: Jun. 24, 2025

(54) OXYGENATOR WITH STACKED FIBER MEMBRANE

(71) Applicant: CardiacAssist, Inc., Pittsburgh, PA (US)

(72) Inventors: William Gesler, New Hudson, MI (US); Michael J. Linehan, Pittsburgh, PA (US); Robert G. Svitek, Freeport, PA (US)

(73) Assignee: CardiacAssist, Inc.

( * ) Notice: Subject to any disclaimer, the term of this patent is extended or adjusted under 35 U.S.C. 154(b) by 657 days.

(21) Appl. No.: 17/686,166

(22) Filed: Mar. 3, 2022

(65) Prior Publication Data
US 2022/0184287 A1 Jun. 16, 2022

Related U.S. Application Data

(63) Continuation of application No. PCT/US2020/052460, filed on Sep. 24, 2020.

(60) Provisional application No. 62/906,603, filed on Sep. 26, 2019.

(51) Int. Cl.
*A61M 1/16* (2006.01)

(52) U.S. Cl.
CPC ........ *A61M 1/1698* (2013.01); *A61M 1/1621* (2014.02); *B01D 2313/205* (2022.08)

(58) Field of Classification Search
CPC .... A61M 1/1698; A61M 1/1621; A61M 1/14; A61M 1/16; A61M 1/30; A61M 1/34; A61M 1/36; B01D 63/026; B01D 63/043; B01D 2313/205
See application file for complete search history.

(56) References Cited

U.S. PATENT DOCUMENTS

| | | | |
|---|---|---|---|
| 2016/0095969 A1* | 4/2016 | Maurer | A61M 1/262 264/263 |
| 2018/0078695 A1 | 3/2018 | Plott et al. | |
| 2018/0117231 A1* | 5/2018 | Matheis | A61M 1/1698 |

FOREIGN PATENT DOCUMENTS

WO 9952621 A1 10/1999

OTHER PUBLICATIONS

International Search Report and Written Opinion for International Application No. PCT/US2020/052460 dated Jan. 19, 2021.

* cited by examiner

*Primary Examiner* — Ariana Zimbouski
*Assistant Examiner* — Timothy L Flynn
(74) *Attorney, Agent, or Firm* — Seager, Tufte & Wickhem LLP

(57) ABSTRACT

A blood oxygenator includes a housing having a first end opposite a second end with a sidewall extending between the first end and the second end along a longitudinal axis. The housing defines an interior chamber having a liquid inlet at the first end and a liquid outlet at the second end. The oxygenator further includes a gas exchange assembly positioned within the interior chamber. The gas exchange assembly includes a retainer having an upper cap spaced apart from a lower cap by one or more spacers, and a gas exchange medium disposed between the upper cap and the lower cap. The gas exchange medium has a plurality of subunits stacked on top of each other, with each subunit having a plurality of layers of hollow fiber mats.

18 Claims, 20 Drawing Sheets

OXYGENATOR WITH STACKED FIBER MEMBRANE

CROSS REFERENCE TO RELATED APPLICATIONS

This application is a continuation of International Application No. PCT/US2020/052460, filed Sep. 24, 2020, which claims the benefit of priority to U.S. Provisional Patent Application Ser. No. 62/906,603, filed on Sep. 26, 2019, titled Oxygenator With Stacked Fiber Membrane, the disclosure of which is incorporated herein by reference.

BACKGROUND OF THE DISCLOSURE

Field of the Disclosure

The present disclosure is generally related to a blood oxygenator configured for use in extracorporeal membrane oxygenation procedures. More specifically, the disclosure relates to a blood oxygenator having a stacked fiber membrane.

Description of Related Art

Blood oxygenators are commonly used to accomplish the gas exchange functions normally performed by the lungs. Conventional blood oxygenators contain a gas exchange medium, such as a filter membrane made from hollow fibers, across which blood is flowed. The filter membrane is connected to an oxygen supply such that oxygen is diffused from the filter membrane into the blood and carbon dioxide is removed from the blood into the filter membrane.

Conventional oxygenators are commonly used in medical situations when a patient's lungs are temporarily disabled and/or incapable of performing their normal function. In some medical situations, blood oxygenators are used as a temporary gas exchange member to substitute or supplement the lung function during, for example, open heart surgery. During such procedures, vital functions of the circulatory system are assumed by an extracorporeal bypass circuit in which a pump sends the patient's blood through a blood oxygenator to deliver oxygen to the patient. In other medical situations, a patient may have an indwelling catheter connected to a pump to deliver blood to a blood oxygenator. In these applications, the oxygenator can be used for an indefinite term.

Membrane blood oxygenators transfer oxygen into the blood as the blood flows over a bundle of hollow fibers having oxygen flowing therethrough. Within the prior art, the bundle of hollow fibers may be formed by rolling a fiber mat around a core to form a spirally-wound bundle or by stacking a plurality of individual fiber layers. In blood oxygenators with stacked fiber layers, gas exchange efficiency can be increased by orienting the fibers between adjacent layers at an angle, such as up to 90 degrees relative to each other. Blood oxygenators having such fiber arrangement have a square outer shape in order to minimize the amount of potting that must be used to isolate the gas path from the blood path. The square shape increases the physical size of the oxygenator. There is a need in the art for an improved blood oxygenator having an increased gas exchange efficiency and a smaller size compared to conventional blood oxygenators having a stacked fiber membrane.

SUMMARY OF THE DISCLOSURE

In some examples or aspects of the present disclosure, an improved blood oxygenator has an increased gas exchange efficiency and a small size. The blood oxygenator may have a housing having a first end opposite a second end with a sidewall extending between the first end and the second end along a longitudinal axis. The housing may define an interior chamber having a liquid inlet at the first end and a liquid outlet at the second end. The oxygenator further may include a gas exchange assembly positioned within the interior chamber. The gas exchange assembly may include a retainer having an upper cap spaced apart from a lower cap by one or more spacers, and a gas exchange medium disposed between the upper cap and the lower cap. The gas exchange medium may have a plurality of subunits stacked on top of each other, with each subunit having a plurality of layers of hollow fiber mats.

In some examples or aspects, the liquid inlet may be formed on a liquid inlet cap enclosing the first end of the housing. The liquid outlet may be formed on a liquid outlet cap enclosing the second end of the housing. The housing may have a circular cross-sectional shape, taken transverse to the longitudinal axis. The upper cap and the lower cap each may have a plurality of openings. The one or more spacers may be a pair of spacers positioned diametrically opposite to each other. The upper cap may be removable from the one or more spacers.

In some examples or aspects, the plurality of subunits may be identical to each other in at least one characteristic. In other examples or aspects, at least one of the plurality of subunits may differ from other subunits in at least one characteristic. The at least one characteristic may be a size of the subunit, a shape of the subunit, a thickness of the subunit, a number of layers of hollow fiber mats, and an angle of orientation of layers of hollow fiber mats.

Various other aspects of the present disclosure are recited in one or more of the following clauses:

Clause 1: A blood oxygenator comprising: a housing having a first end opposite a second end with a sidewall extending between the first end and the second end along a longitudinal axis, the housing defining an interior chamber having a liquid inlet at the first end and a liquid outlet at the second end; and a gas exchange assembly positioned within the interior chamber, the gas exchange assembly comprising: a retainer having an upper cap spaced apart from a lower cap by one or more spacers; and a gas exchange medium disposed between the upper cap and the lower cap, wherein the gas exchange medium comprises a plurality of subunits stacked on top of each other, each subunit comprising a plurality of layers of hollow fiber mats.

Clause 2. The blood oxygenator of clause 1, wherein the liquid inlet is formed on a liquid inlet cap enclosing the first end of the housing.

Clause 3. The blood oxygenator of clause 1 or 2, wherein the liquid outlet is formed on a liquid outlet cap enclosing the second end of the housing.

Clause 4. The blood oxygenator of any of clauses 1-3, wherein the housing has a circular cross-sectional shape.

Clause 5. The blood oxygenator of any of clauses 1-4, wherein the upper cap and the lower cap each have a plurality of openings.

Clause 6. The blood oxygenator of any of clauses 1-5, wherein the one or more spacers is a pair of spacers positioned diametrically opposite to each other.

Clause 7. The blood oxygenator of any of clauses 1-6, wherein the upper cap is removable from the one or more spacers.

Clause 8. The blood oxygenator of any of clauses 1-7, wherein the plurality of subunits are identical to each other in at least one characteristic.

Clause 9. The blood oxygenator of clause 8, wherein the plurality of subunits are identical to each other in all characteristics.

Clause 10. The blood oxygenator of clause 8, wherein the at least one characteristic is a size of the subunit, a shape of the subunit, a thickness of the subunit, a number of layers of hollow fiber mats, and an angle of orientation of layers of hollow fiber mats.

Clause 11. The blood oxygenator of any of clauses 1-8, wherein at least one of the plurality of subunits differs from other subunits in at least one characteristic.

Clause 12. The blood oxygenator of clause 11, wherein the at least one characteristic is a size of the subunit, a shape of the subunit, a thickness of the subunit, a number of layers of hollow fiber mats, and an angle of orientation of layers of hollow fiber mats.

Clause 13. The blood oxygenator of any one of clauses 1-12, wherein the plurality of subunits are elliptical in shape.

Clause 14. The blood oxygenator of clause 13, wherein the plurality of subunits are stacked offset from one another such that an axis extending through the centroid of each of the subunits is at an angle relative to the longitudinal axis of the housing.

Clause 15. The blood oxygenator of clause 14, wherein the angle is between 20 degrees and 45 degrees.

Clause 16. A blood oxygenator including a housing having a first end opposite a second end with a sidewall extending between the first end and the second end along a longitudinal axis. The housing defines an interior chamber having a liquid inlet at the first end and a liquid outlet at the second end. A gas exchange assembly is positioned within the interior chamber. The gas exchange assembly includes a gas exchange medium disposed within the interior chamber. The gas exchange medium includes a plurality of subunits stacked on top of each other, each subunit lying in a plane at an acute angle to the longitudinal axis.

Clause 17. The blood oxygenator of clause 16, wherein each subunit comprises a plurality of layers of hollow fiber mats.

Clause 18. The blood oxygenator of clause 16 or 17, wherein the gas exchange chamber has an elliptical shape taken in a plane at an acute angle to the longitudinal axis.

Clause 19. The blood oxygenator of clause 18, wherein each of the plurality of subunits has an elliptical shape.

Clause 20. The blood oxygenator of any one of claims 16-19, wherein the plurality of subunits are stacked offset from one another such that an axis extending through the centroid of each of the subunits is at an acute angle relative to the longitudinal axis of the housing.

Further details and advantages of the various examples or aspects described in detail herein will become clear upon reviewing the following detailed description of the various examples in conjunction with the accompanying drawing figures.

DETAILED DESCRIPTION

Figure 1:
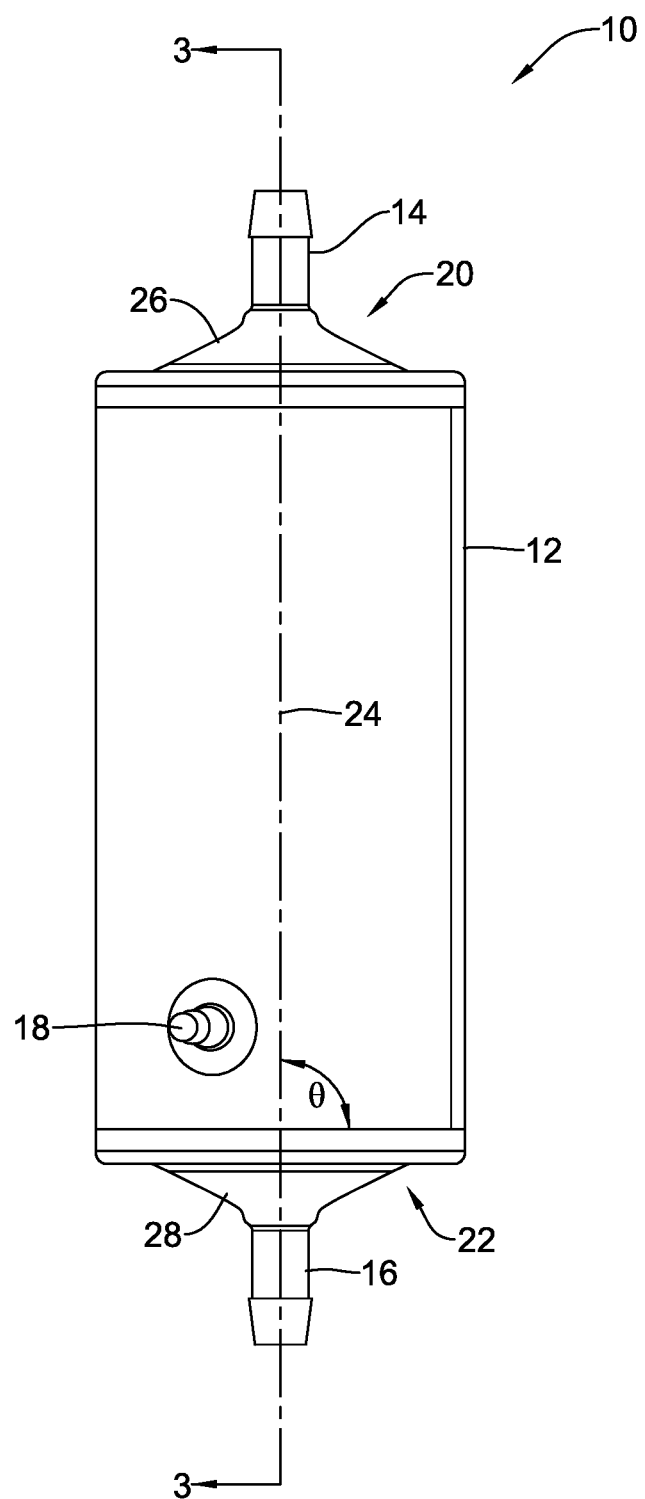
FIG. 1 is a side view of a blood oxygenator in accordance with some examples or aspects of the present disclosure.

The illustrations generally show preferred and non-limiting examples or aspects of the apparatus and methods of the present disclosure. While the description presents various aspects of the apparatus, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described examples contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

As used herein, the terms "parallel" or "substantially parallel" mean a relative angle as between two objects (if extended to theoretical intersection), such as elongated objects and including reference lines, that is from 0° to 5°, or from 0° to 3°, or from 0° to 2°, or from 0° to 1°, or from 0° to 0.5°, or from 0° to 0.25°, or from 0° to 0.1°, inclusive of the recited values.

As used herein, the term "perpendicular" or "substantially perpendicular" mean a relative angle as between two objects (if extended to theoretical intersection), such as elongated objects and including reference lines, that is from 85° to 90°, or from 87° to 90°, or from 88° to 90°, or from 89° to 90°, or from 89.5° to 90°, or from 89.75° to 90°, or from 89.9° to 90°, inclusive of the recited values.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

It should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances. Further, in this application, the use of "a" or "an" means "at least one" unless specifically stated otherwise.

Referring to FIG. 1, a blood oxygenator 10 is shown in accordance with one example or aspect of the present disclosure. The blood oxygenator 10 may be suitable for use in an extracorporeal membrane oxygenation (ECMO) system. The blood oxygenator 10 has a housing 12 having a liquid inlet 14, a liquid outlet 16, a gas inlet 18, and a gas outlet 19 (shown in FIG. 2). The housing 12 has a first end 20 opposite a second end 22 extending along a longitudinal axis 24. A liquid inlet cap 26 is provided at the first end 20 of the housing 12, with the liquid inlet 14 extending through the liquid inlet cap 26. A liquid outlet cap 28 is provided at the second end 22 of the housing 12, with the liquid outlet 16 extending through the liquid outlet cap 28. The liquid inlet cap 26 and the liquid outlet cap 28 may be shaped to prevent velocity change of the blood as the blood enters or exits the oxygenator 10. For example, the liquid inlet cap 26 and the liquid outlet cap 28 may have a radial draft to prevent eddy flow and recirculation of blood.

In some examples or aspects, the liquid inlet 14 and/or the liquid outlet 16 may be coaxially arranged with the longitudinal axis 24. In other examples or aspects, the liquid inlet 14 and/or the liquid outlet 16 may be offset relative to the longitudinal axis 24, extending parallel to the longitudinal axis 24 or at an angle relative to the longitudinal axis 24. The liquid inlet 14 and the liquid outlet 16 may have a barbed fitting for facilitating connection of a liquid inlet cannula and a liquid outlet cannula, respectively. In some examples or aspects, the liquid inlet cannula may be connected to an outlet of a blood pump for delivering blood withdrawn from the patient's body to the oxygenator 10 via the blood pump. The liquid outlet cannula may be configured to deliver oxygenated blood to the patient's body after the blood has been oxygenated by passing through the oxygenator 10.

Figure 2:
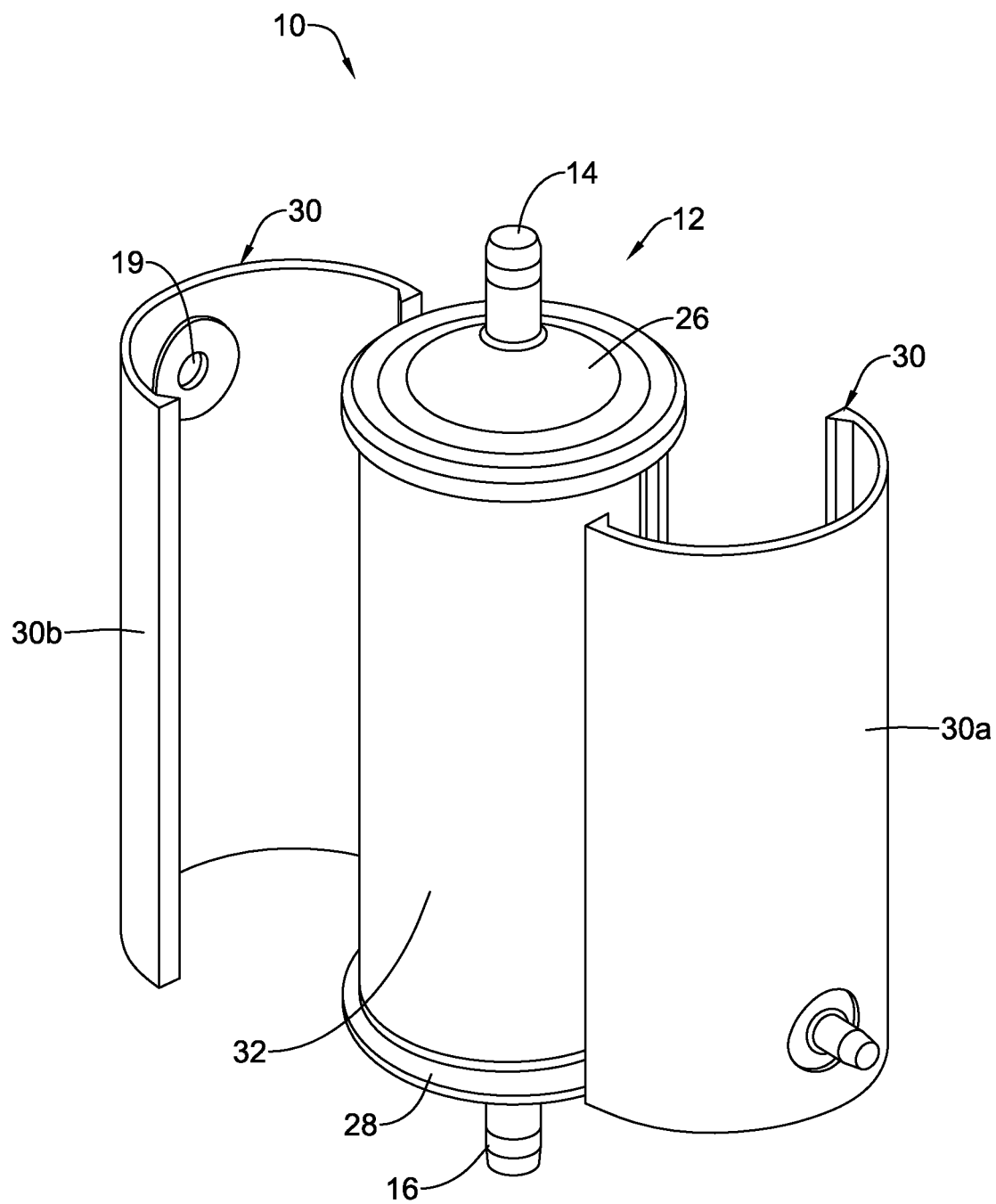
FIG. 2 is an exploded top perspective view of the blood oxygenator shown in FIG. 1.

With reference to FIG. 2, the housing 12 has at least one gas cap 30 between the liquid inlet cap 26 and the liquid outlet cap 28. The at least one gas cap 30 defines the sidewall of the housing between the liquid inlet cap 26 and the liquid outlet cap 28. In some examples or aspects, such as shown in FIG. 2, the at least one gas cap 30 can be a pair of gas caps 30a, 30b that are configured to connect to each other along their longitudinal length in a liquid-tight sealing manner. Upper and lower portions of the at least one gas cap 30 are configured to connect to the liquid inlet cap 26 and the liquid outlet cap 28, respectively, in a liquid-tight sealing manner. For example, as shown in FIG. 3, the liquid inlet cap 26 and the liquid outlet cap 28 may have grooves 31 configured to receive a projection 33 on upper and lower ends of the at least one gas cap 30.

With continued reference to FIG. 2, a first gas cap 30a may have the gas inlet 18 extending therethrough, while the second gas cap 30b may have the gas outlet 19 extending therethrough. The gas inlet 18 and the gas outlet 19 may have a barbed fitting for facilitating connection of a gas inlet hose and a gas outlet hose, respectively. The gas inlet 18 may be in fluid communication with a gas source, such as a tank of medical-grade oxygen gas.

With continued reference to FIG. 2, the housing 12 may have a circular or oval cross-sectional shape and may be made from a rigid material, such as a biocompatible plastic. The plastic may be transparent, translucent, or opaque.

Figure 3:
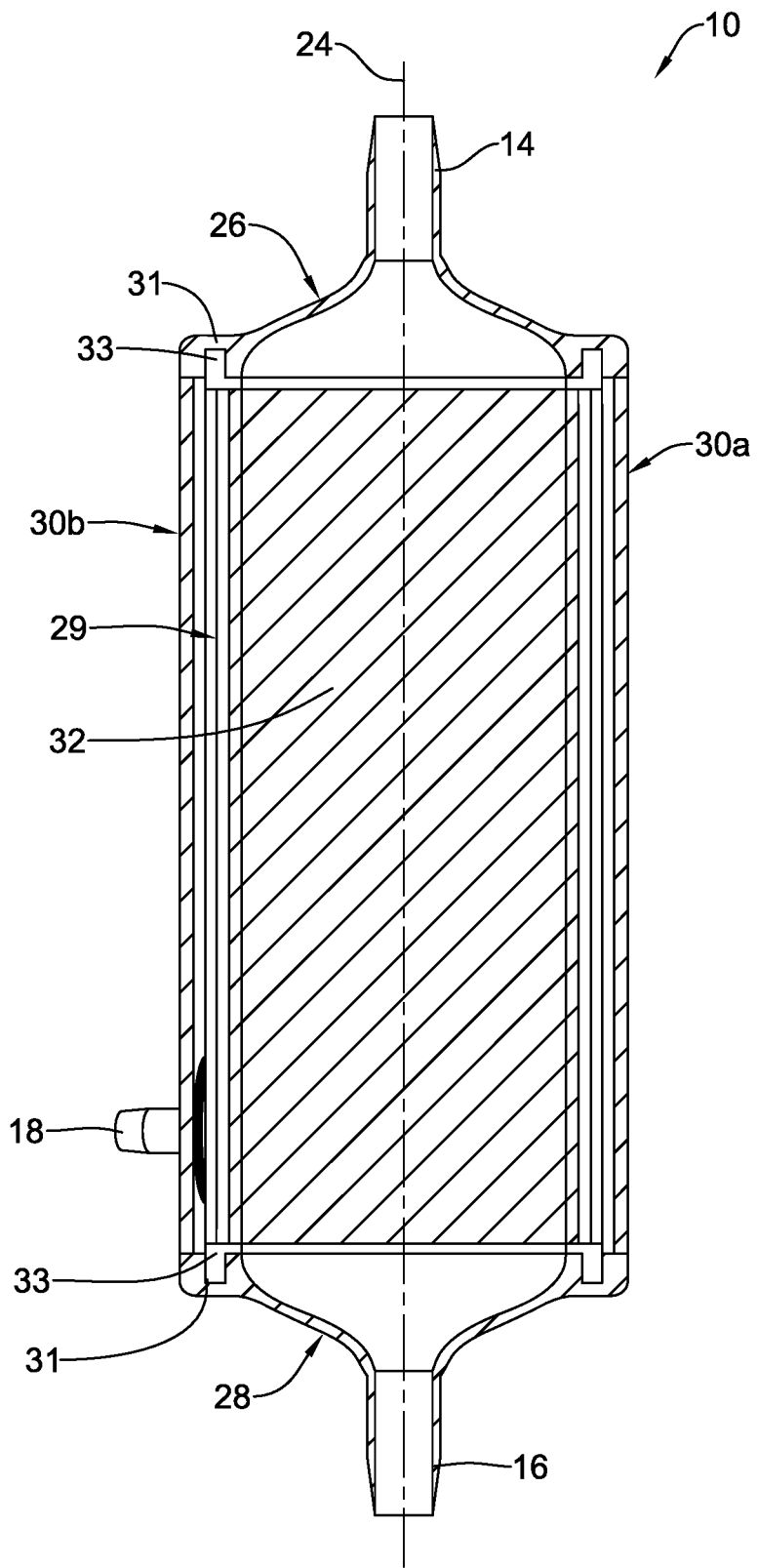
FIG. 3 is a cross-sectional view of the blood oxygenator shown in FIG. 1 taken along line 3-3.

With reference to FIG. 3, the liquid inlet cap 26, the liquid outlet cap 28, and the gas cap 30 together enclose an interior chamber 29 that provides the space in which gas exchange functions are performed via a gas exchange assembly 32, as described herein. The gas inlet 18 and the gas outlet 19 are in fluid communication with each other via a gas flow path through a plurality of fibers of the gas exchange assembly 32. The liquid inlet 14 and the liquid outlet 16 are in fluid communication with each other via a blood flow path extending between the fibers of the gas exchange assembly 32.

Figure 4:
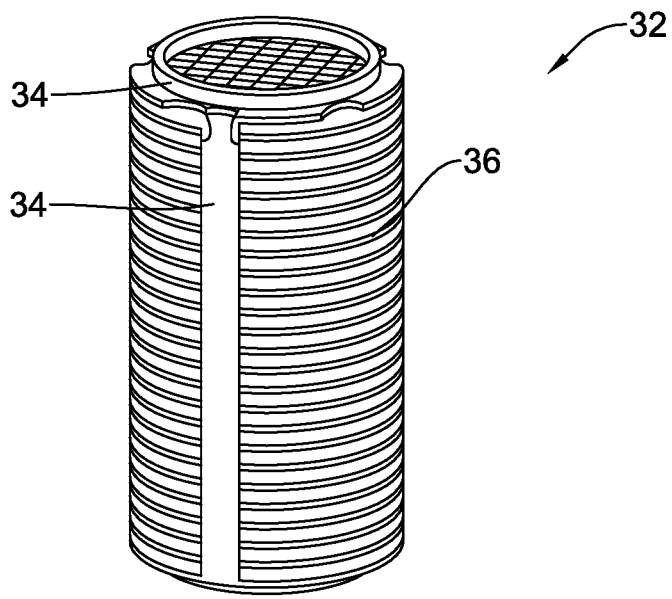
FIG. 4 is a top perspective view of a gas exchange assembly for use with the blood oxygenator of FIG. 1, with the gas exchange assembly shown prior to potting.
Figure 5:
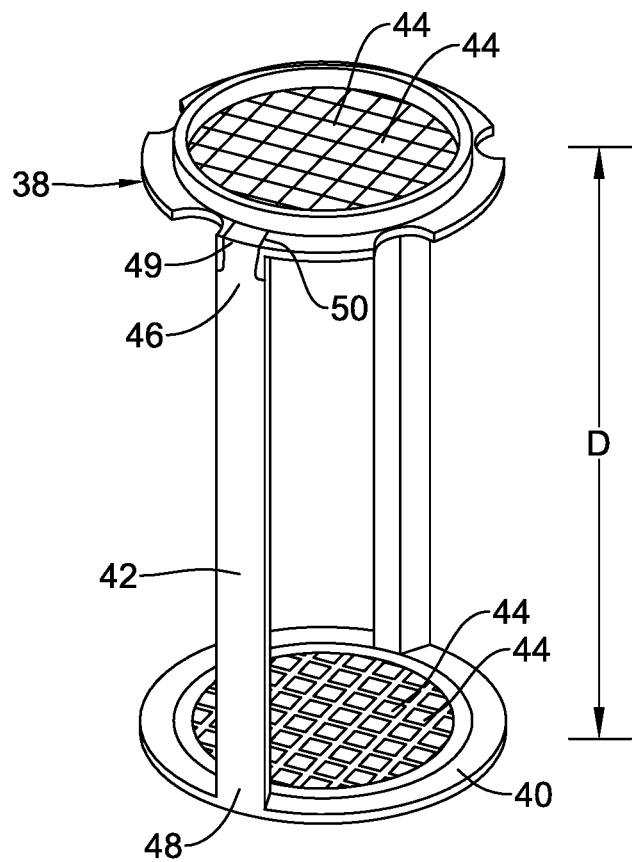
FIG. 5 is a top perspective view of a retainer of a gas exchange assembly shown in FIG. 4.

With reference to FIG. 4, the gas exchange assembly 32 is shown separate from the oxygenator 10 and prior to being potted with a potting material. The gas exchange assembly 32 includes a retainer 34 configured to hold a gas exchange medium 36. The retainer 34 holds the gas exchange medium 36 and maintains the spacing between individual subunits of the gas exchange medium 36 prior to potting, as described herein. As shown in FIG. 5, the retainer has an upper cap 38 spaced apart from a lower cap 40 by one or more spacers 42. The upper cap 38 is shaped to be received within the interior chamber 29 of the housing 12 (shown in FIG. 3) such that the upper cap 38 is positioned proximate to the liquid inlet cap 26. Similarly, the lower cap 40 is shaped to be received within the interior chamber 29 of the housing 12 such that the lower cap 40 is positioned proximate to the liquid outlet cap 28. In some examples or aspects, the upper cap 38 and the lower cap 40 have a substantially circular shape that corresponds to a circular shape of the interior chamber 29 of the housing 12.

With continued reference to FIG. 5, the upper cap 38 and the lower cap 40 each have a plurality of openings 44 configured to allow liquid to flow from one side of the upper cap 38 and the lower cap 40 to the opposing side of the upper cap 38 and the lower cap 40. In this manner, blood entering the oxygenator 10 through the liquid inlet 14 (shown in FIG. 3) passes through the openings 44 on the upper cap 38 to get to the gas exchange medium 36. After becoming oxygenated via diffusion of oxygen flowing through the fibers of the gas exchange medium 36 into the blood, the blood passes through the openings 44 on the lower cap 40 before exiting the oxygenator 10 through the liquid outlet 16 (shown in FIG. 3). The size, shape, and arrangement of openings 44 is selected to minimize pressure loss between the liquid inlet 14 and the liquid outlet 16.

With continued reference to FIG. 5, the one or more spacers 42 of the retainer 34 may be a pair of spacers 42 positioned diametrically opposite to each other. The spacers 42 may be positioned at an outer edge of the upper cap 38 and the lower cap 40 and are configured to maintain the upper cap 38 and the lower cap 40 spaced apart from each other by a predetermined distance D. The spacers 42 may extend substantially parallel with the longitudinal axis 24 of the oxygenator 10 (shown in FIG. 3). In some examples or aspects, each of the one or more spacers 42 has a first end 46 that is connected to the upper cap 38 and an opposing second end 48 that is connected to the lower cap 40. The one or more spacers 42 may be removably or non-removably connected to the upper cap 38 and the lower cap 40. In some examples or aspects, such as shown in FIG. 5, the one or more spacers 42 may be removably connected to the upper cap 38 and monolithically formed with the lower cap 40. The first end 46 of each spacer 42 may have a first connector 49 that is configured to be removably connected to a corresponding second connector 50 on the upper cap 38. In some examples or aspects, the first and second connectors 49, 50 may be tongue and groove connectors.

Figure 6:
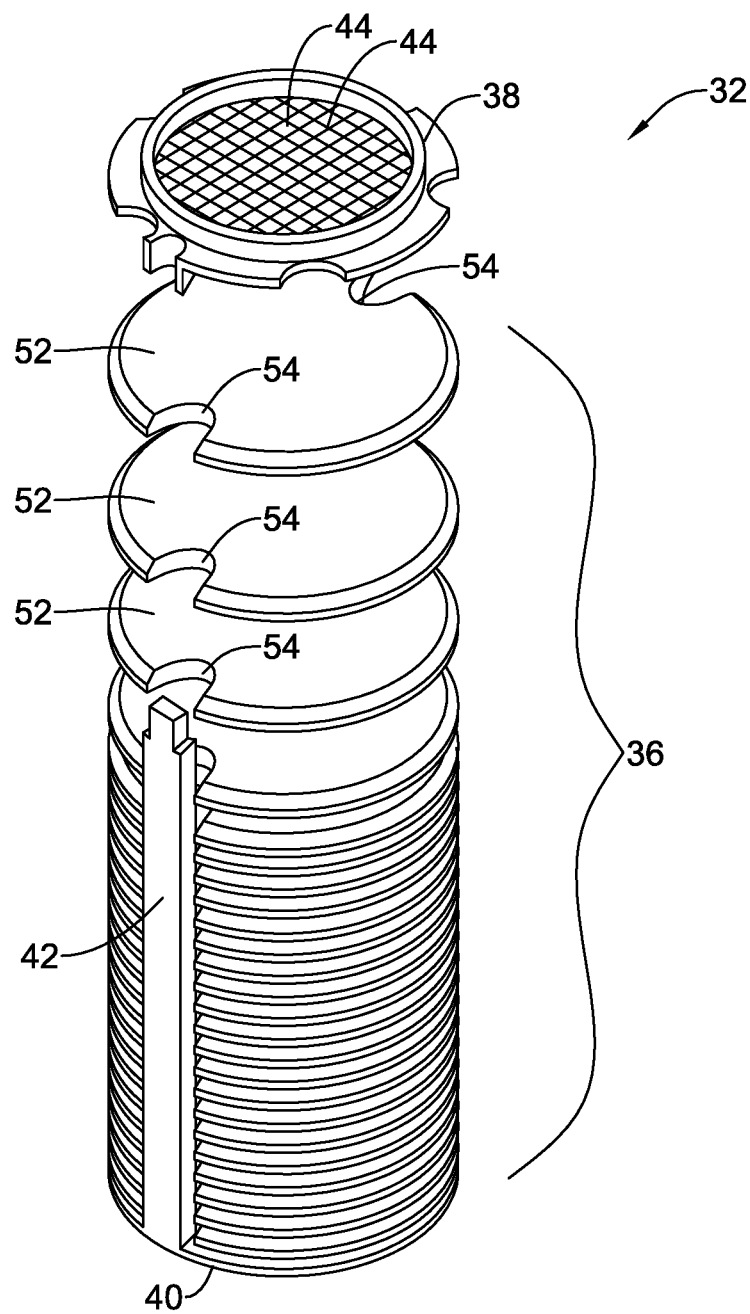
FIG. 6 is a partially exploded top perspective view of the gas exchange assembly shown in FIG. 4.

With reference to FIG. 6, the gas exchange medium 36 is disposed within the space between the upper cap 38 and the lower cap 40. The gas exchange medium 36 is configured for diffusing a gas flowing therethrough into the liquid flowing around the gas exchange medium 36. In some examples or aspects, the gas exchange medium 36 has a plurality of subunits 52 that are stacked on top each other between the upper cap 38 and the lower cap 40. Each subunit 52 is made up of a plurality of layers of fiber mats, with each fiber mat having a plurality of individual hollow fibers. The fibers are configured to carry a gas, such as oxygen, in such a manner that allows the gas to be taken up by a liquid, such as blood, flowing around the fibers, and to absorb any other gas given off by the liquid, such as carbon dioxide. The gas exchange medium 36 provides the required surface area for the gas exchange to occur.

In some examples or aspects, the plurality of subunits 52 may be identical to each other in at least one characteristic, such as size, shape, thickness, number of layers of fibers mats, type of fiber mats, and orientation of layers of fiber mats relative to each other. In other examples or aspects, at least one of the plurality of subunits 52 may differ from other subunits in at least one characteristic, such as size, shape, thickness, number of layers of fibers mats, type of fiber mats, and orientation of layers of fiber mats relative to each other. For example, the number of layers of fiber mats in each subunit 52 may vary such that a thickness of the subunits 52 varies. The thickness of the subunits 52 may be varied progressively along the length of the gas exchange medium 36 between the upper cap 38 and the lower cap 40 of the retainer 34.

With continued reference to FIG. 6, each subunit 52 of the gas exchange medium 36 may have a substantially circular shape that corresponds to the circular shape of the upper cap 38 and the lower cap 40 of the retainer 34. Each subunit 52 may have one or more notches 54 configured to receive at least a portion of the corresponding one or more spacers 42. In this manner, rotation of the subunits 52 about the longitudinal axis of the gas exchange medium 36 can be prevented in order to maintain a desired orientation of the hollow fibers between adjacent subunits 52.

Figure 7:
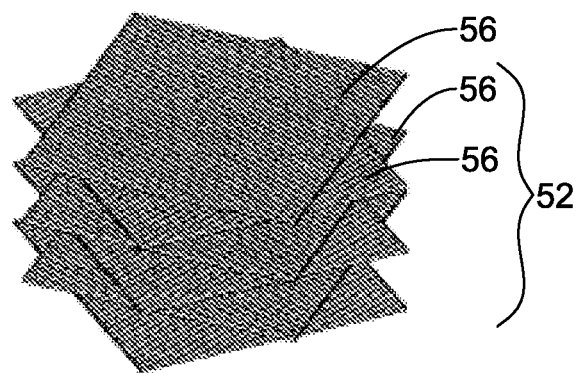
FIG. 7 is a top perspective view of a plurality of stacked fiber membranes for use in a gas exchange assembly in accordance with some examples or aspects of the present disclosure.
Figure 8:
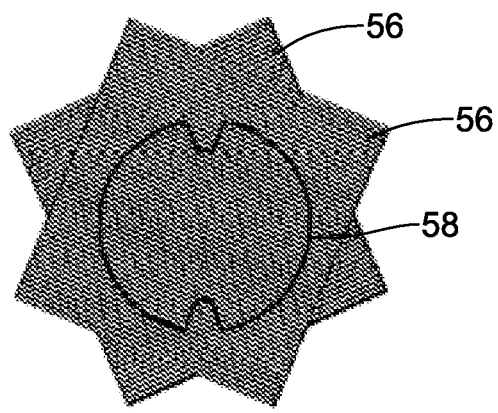
FIG. 8 is a top view of the plurality of stacked fiber membranes shown in FIG. 7 with a shape of a cutout die superimposed on a top fiber membrane.
Figure 9:
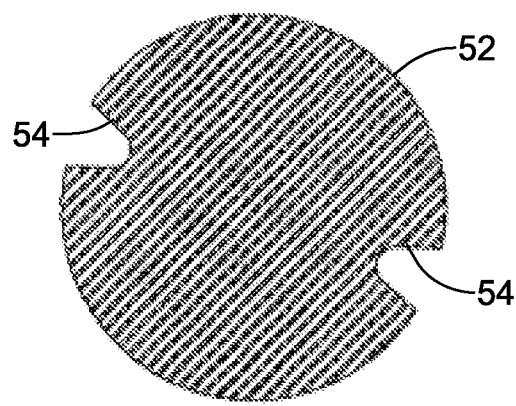
FIG. 9 is a top view of a subunit of a gas exchange medium for use with a gas exchange assembly.

With reference to FIG. 7, each subunit 52 is made by stacking a plurality of individual fiber mats 56 on top of each other. The individual fiber mats 56 may be arranged such that they are angled relative to one another, such as by 0 to 90 degrees between adjacent layers of fiber mats 56, or by 10 to 80 degrees between adjacent layers of fiber mats 56, or by 20 to 70 degrees between adjacent layers of fiber mats 56, or by 30 to 60 degrees between adjacent layers of fiber mats 56, or by 40 to 50 degrees between adjacent layers of fiber mats 56, or by about 45 degrees between adjacent layers of fiber mats 56. As shown in FIG. 8, the stack of fiber mats 56 is then cut into a shape of the subunit 52 using a die 58. In some examples or aspects, cutting of the stack of fiber mats 56 into the shape of the subunit 52 (FIG. 9) may seal the outside edge of the fiber mats 56 together such that the fiber mats 56 are not separable from each other after cutting. A plurality of subunits 52 may then be stacked in the retainer 34. After stacking the plurality of subunits 52 into the retainer 34, upper cap 38 is connected to the spacers 42 to enclose the plurality of subunits 52 between the upper cap 38 and the lower cap 40, thereby completing a stacked gas exchange assembly 32.

The gas exchange assembly 32 is then placed into a potting cup and a potting material poured into the cup while the cup is rotated about its longitudinal axis. Due to a centrifugal force, the potting material accumulates and solidifies at an outer edge of the gas exchange assembly 32. After potting, the gas exchange assembly 32 is taken out of the potting cup and is trimmed by cutting away the potting material to expose the openings to the individual hollow fibers of the fiber mats. The potting material that surrounds the openings of the individual hollow fibers seals the hollow fibers of the gas exchange medium 36 in order to prevent direct mixing of the gas flowing through the hollow fibers with the liquid flowing around the hollow fibers.

In some examples or aspects, the gas exchange assembly 32 may be trimmed to have a uniform outer diameter along its longitudinal length. In this manner, the length of the gas path of individual fibers is constant along the length of the gas exchange medium 36. In other examples or aspects, the gas exchange assembly 32 may be trimmed to have a non-uniform outer diameter along its longitudinal length. For example, the gas exchange assembly 32 may be sloped such that its diameter increases or decreases along its longitudinal length. In this manner, the length of the gas path of individual fibers is a function of the slope of the gas exchange assembly 32. Regions with thicker potting have a reduced cross-sectional flow area compared to regions with thinner potting, which allows for increased blood velocity and decrease in boundary layer thickness to aid in gas exchange rate in such regions. After trimming, the gas exchange assembly 32 is inserted into the interior chamber 29 of the housing 12 and the liquid inlet and outlet caps 26, 28 are sealed with the gas caps 30 to define a finished oxygenator 10.

Figure 10:
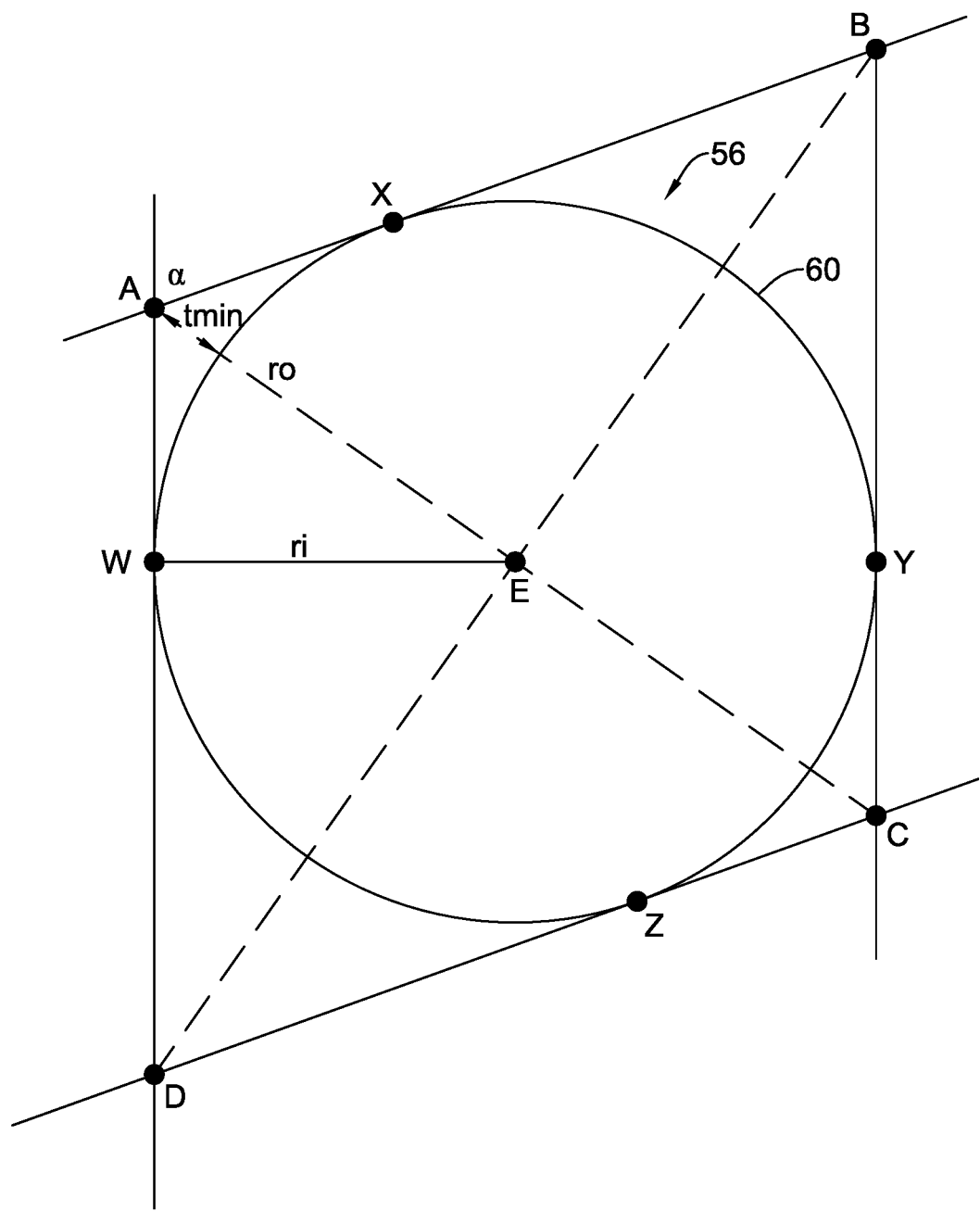
FIG. 10 is a schematic diagram showing a minimum potting thickness of a gas exchange medium as a function of an overlap angle between layers of stacked fiber membranes.

With reference to FIG. 10, a schematic diagram shows a minimum potting thickness for the gas exchange medium 36 as a function of an overlap angle between layers of stacked fiber mats 56. In this exemplary diagram, each fiber mat 56 has a circular shape with a radius $r_t$ and a center E. Given an angle α between adjacent layers of fiber mats 56, a first flow path through the first layer of fiber mats 56 is defined in a direction between points A and C, and a second flow path through the second layer of fiber mats 56 is defined in a direction between points B and D. A quadrilateral that connects points A, B, C, and D has tangential points W, X, Y, and Z with the outer surface 60 of the fiber mats 56. A distance between point A and the outer surface 60 of the fiber mats 56 represents a minimum thickness $t_{min}$ of the potting material that must be used in order to isolate the gas path extending through the hollow fibers of the gas exchange medium 36 from the blood path extending around the hollow fibers of the gas exchange medium 36. In other words, the minimum thickness $t_{min}$ of the potting material can be expressed as a difference between an outer radius $r_o$ defined by point A and the inner radius $r_i$ defined by the outer surface 60 of the fiber mats 56. The minimum thickness $t_{min}$ may be calculated using the following formula:

$$t_{min} = \frac{r_i - r_i\left(\sin\left(\frac{180-\alpha}{2}\right)\right)}{\sin\left(\frac{180-\alpha}{2}\right)}$$

Figure 11:
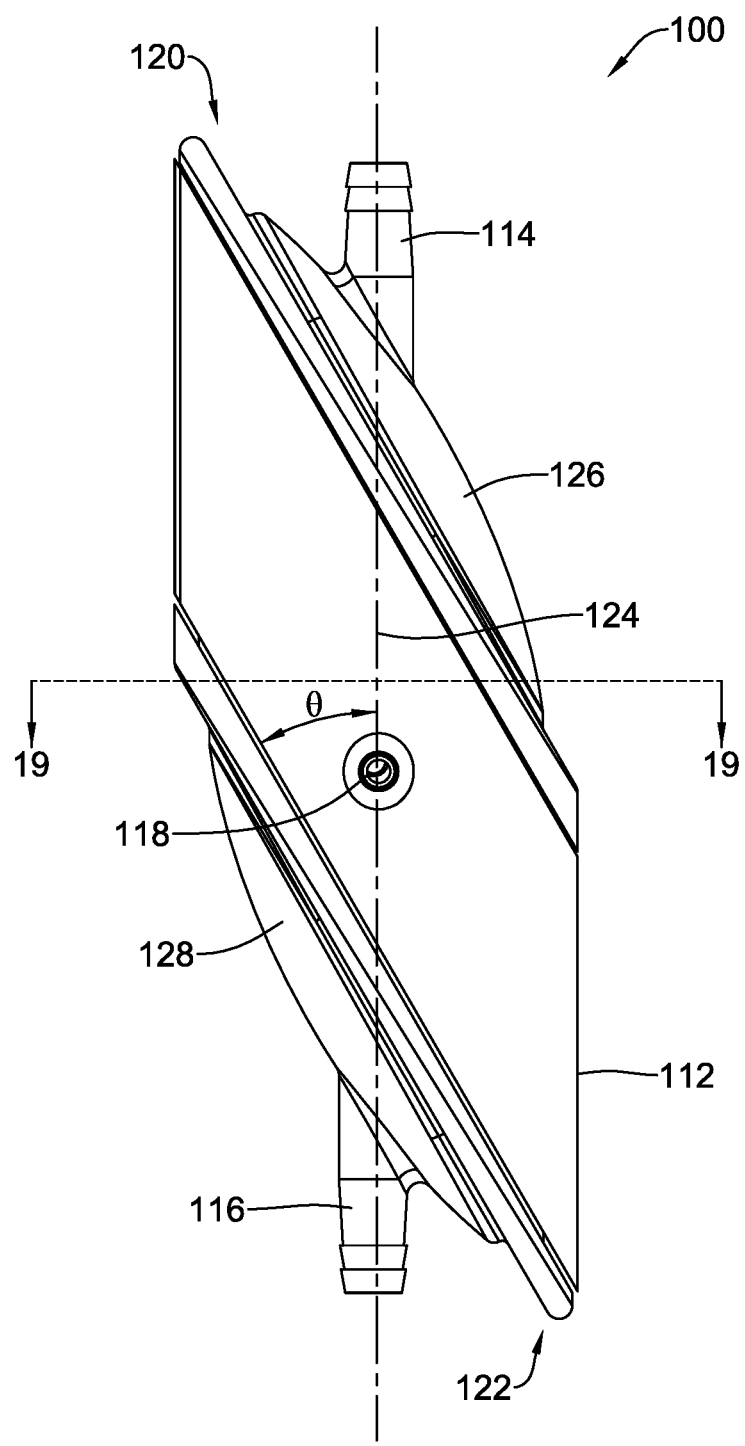
FIG. 11 is a side view of a blood oxygenator in accordance with another example or aspect of the present disclosure.

With reference to FIG. 11, an alternative blood oxygenator 100 is shown in accordance with another example or aspect of the present disclosure. Unless specifically stated otherwise, the blood oxygenator 100 includes all elements of the blood oxygenator 10 described above. The blood oxygenator 100 differs from the blood oxygenator 10 in the shape of the housing 112 and gas exchange medium 136, but the two blood oxygenators 10, 100 function in the same manner.

Figure 13:
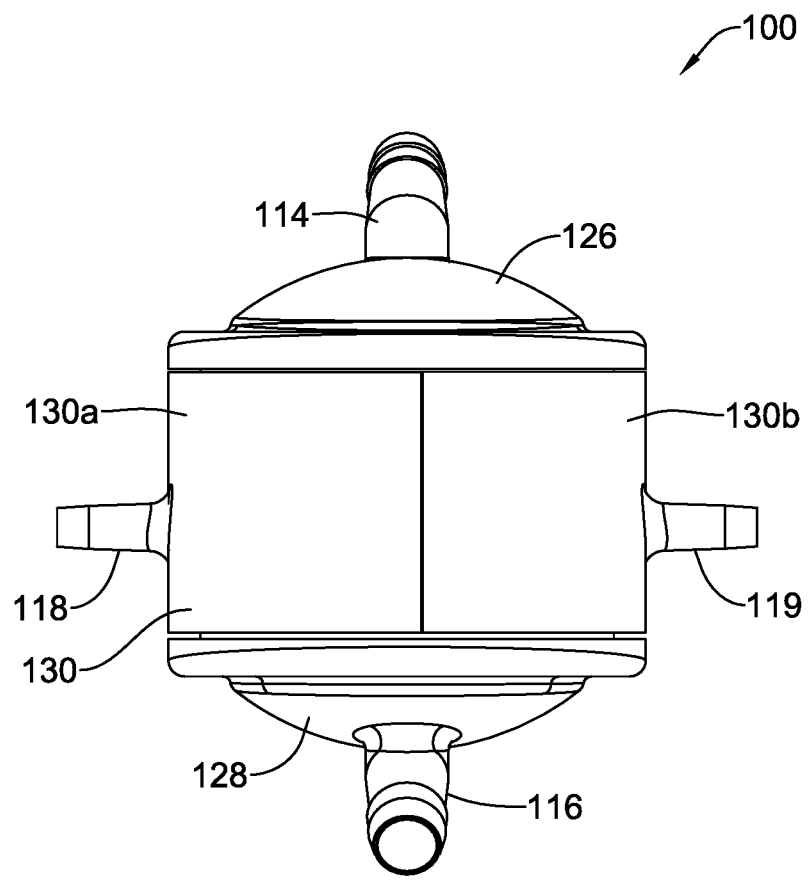
FIG. 13 is a tilted side view of the blood oxygenator shown in FIG. 11.

The blood oxygenator 100 has a housing 112 having a liquid inlet 114, a liquid outlet 116, a gas inlet 118, and a gas outlet 119 (shown in FIG. 13). The housing 112 has a first end 120 opposite a second end 122 extending along a longitudinal axis 124. A liquid inlet cap 126 is provided at the first end 120 of the housing 112, with the liquid inlet 114 extending through the liquid inlet cap 126. A liquid outlet cap 128 is provided at the second end 122 of the housing 112, with the liquid outlet 116 extending through the liquid outlet cap 128.

In some examples or aspects, the liquid inlet 114 and/or the liquid outlet 116 may be coaxially arranged with the longitudinal axis 124. In other examples or aspects, the liquid inlet 114 and/or the liquid outlet 116 may be offset relative to the longitudinal axis 124, extending parallel to the longitudinal axis 124 or at an angle relative to the longitudinal axis 124. The liquid inlet 114 and the liquid outlet 116 may have a barbed fitting for facilitating connection of a liquid inlet cannula and a liquid outlet cannula, respectively. In some examples or aspects, the liquid inlet cannula may be connected to an outlet of a blood pump for delivering blood withdrawn from the patient's body to the oxygenator 100 via the blood pump. The liquid outlet cannula may be configured to deliver oxygenated blood to the patient's body after the blood has been oxygenated by passing through the oxygenator 100.

Figure 12:
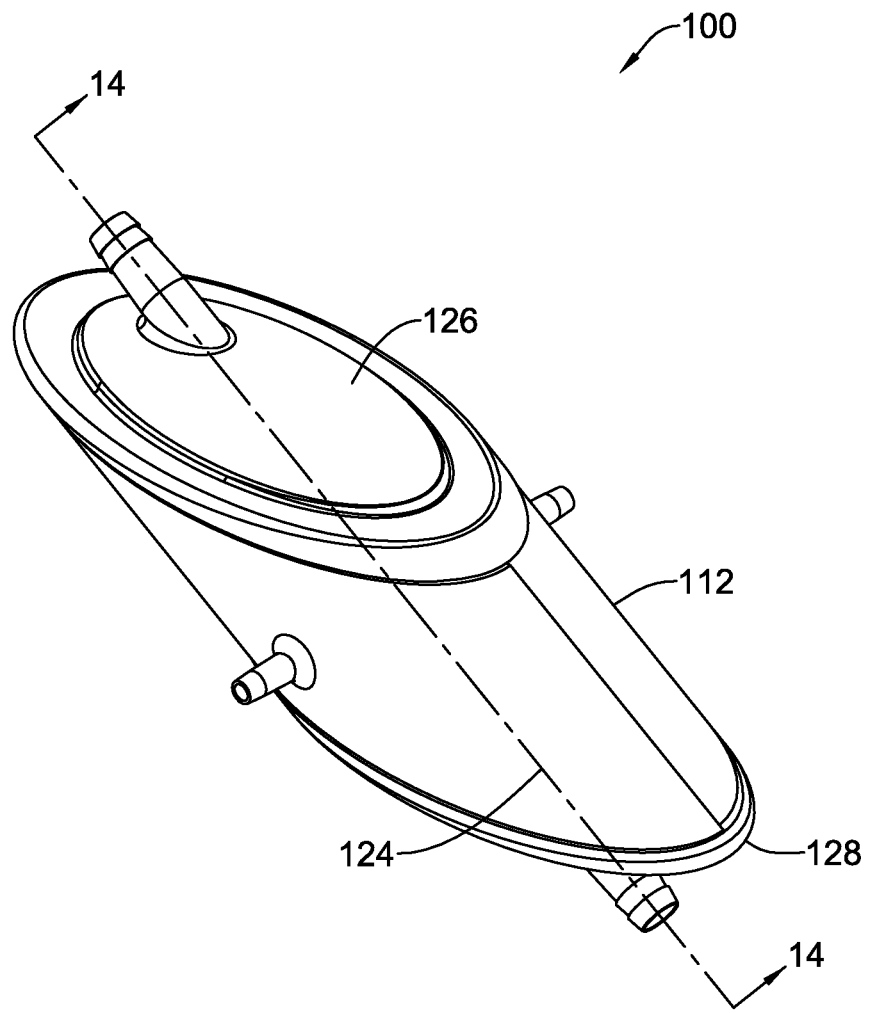
FIG. 12 is a perspective view of the blood oxygenator shown in FIG. 11.

The housing 112 of the oxygenator 100 is angled relative to the longitudinal axis 124, as shown in FIG. 11. The angle Θ is measured between the longitudinal axis 124 extending through the liquid inlet 114 and the liquid outlet 116, and the plane that the base of the liquid outlet cap 128 lies in. The plane that the base of the liquid inlet cap 126 lies in may also be at the angle Θ from the longitudinal axis 124. The housing 112 may be at an angle Θ between 20 and 90 degrees relative to the longitudinal axis. In other words, the rim of the liquid inlet cap 126 may lie in a plane at an angle Θ relative to the longitudinal axis 24 and/or the rim of the liquid outlet cap 128 may lie in a plane at an angle Θ relative to the longitudinal axis 24. The housing 12 of the oxygenator 10 shown in FIGS. 1-3 is at an angle Θ of 90 degrees relative to the longitudinal axis 24. In other examples, the housing may be skewed at an acute angle of less than 90 degrees, such as between 10 degrees and 80 degrees, between 20 degrees and 70 degrees, between 20 degrees and 60 degrees, between 20 degrees and 45 degrees, 20 degrees, 30 degrees, or 45 degrees. In the example shown in FIGS. 11-15, the housing 112 is skewed at an acute angle Θ of 30 degrees relative to the longitudinal axis 124. In addition to being skewed relative to the longitudinal axis, the shape of the liquid inlet cap 126 and the liquid outlet cap 128 may be an ellipse, as shown in FIG. 12. Furthermore, the shape of the cross-section of the housing 112 between liquid inlet cap 126 and the liquid outlet cap 128 taken in a plane perpendicular to the longitudinal axis 124 may also be elliptical. The housing 112 may be made from a rigid material, such as a biocompatible plastic. The plastic may be transparent, translucent, or opaque.

With reference to FIG. 13, the housing 112 has at least one gas cap 130 defining the sidewall of the housing 112 between the liquid inlet cap 126 and the liquid outlet cap 128. In some examples or aspects, such as shown in FIG. 13, the at least one gas cap 130 can be a pair of gas caps 130a, 130b that are configured to connect to each other along their longitudinal length in a liquid-tight sealing manner. Upper and lower portions of the at least one gas cap 130 are configured to connect to the liquid inlet cap 126 and the liquid outlet cap 128, respectively, in a liquid-tight sealing manner.

With continued reference to FIG. 13, a first gas cap 130a may have the gas inlet 118 extending therethrough, while the second gas cap 130b may have the gas outlet 119 extending therethrough. The gas inlet 118 and the gas outlet 119 may have a barbed fitting for facilitating connection of a gas inlet hose and a gas outlet hose, respectively. The gas inlet 118 may be in fluid communication with a gas source, such as a tank of medical-grade oxygen gas.

Figure 14:
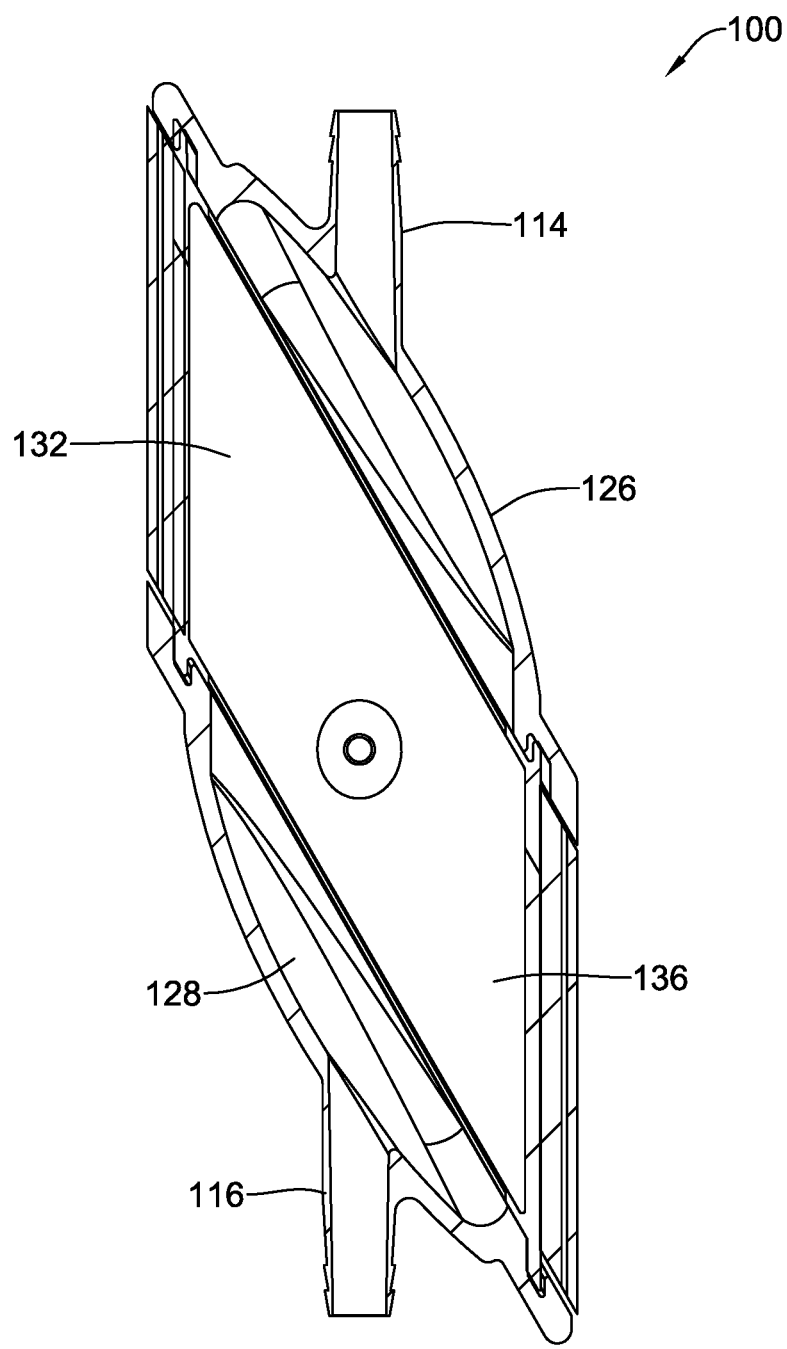
FIG. 14 is a cross-sectional view of the blood oxygenator shown in FIG. 12 taken along line 14-14.

With reference to FIG. 14, the liquid inlet 114 and the liquid outlet 116 are in fluid communication with each other via a blood flow path extending between the fibers of the gas exchange medium 136 in the gas exchange assembly 132. The gas inlet 118 and the gas outlet 119 are in fluid communication with each other via a gas flow path through a plurality of fibers of the gas exchange assembly 132.

Figure 15:
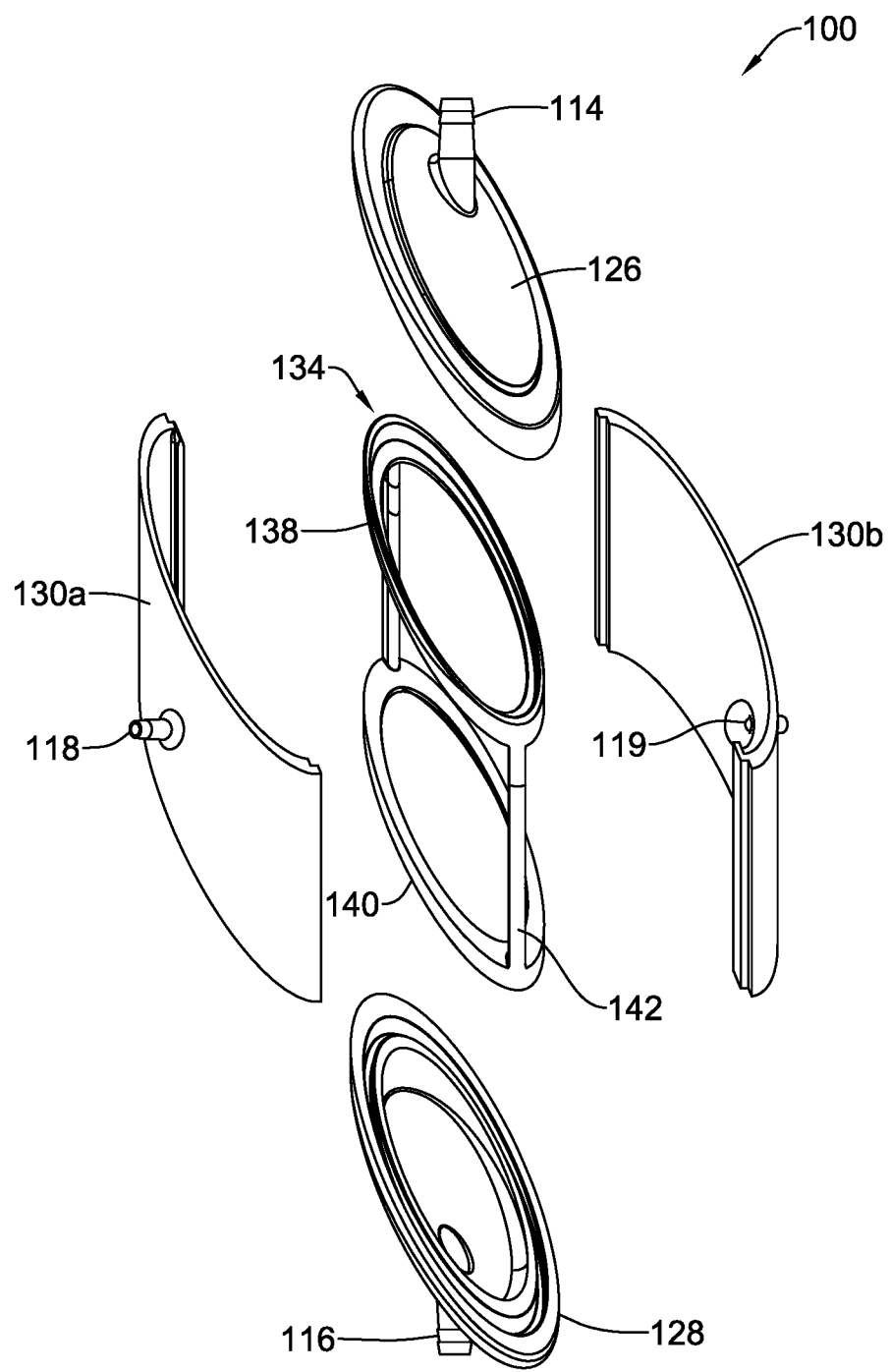
FIG. 15 is an exploded top perspective view of the blood oxygenator shown in FIG. 11, with the gas exchange medium removed.

With reference to FIG. 15, the elements of the oxygenator 100 are shown in an exploded view, with the gas exchange medium removed. The gas exchange assembly includes a retainer 134 configured to hold a gas exchange medium (not shown). The retainer 134 holds the gas exchange medium and maintains the spacing between individual subunits of the gas exchange medium prior to potting, as described above. As shown in FIG. 15, the retainer 134 has an upper cap 138 spaced apart from a lower cap 140 by one or more spacers 142. The upper cap 138 is shaped to be received within the interior chamber of the housing 112 such that the upper cap 138 is positioned proximate to the liquid inlet cap 126. Similarly, the lower cap 140 is shaped to be received within the interior chamber of the housing 112 such that the lower cap 140 is positioned proximate to the liquid outlet cap 128. In some examples or aspects, the upper cap 138 and the lower cap 140 have a substantially elliptical shape that corresponds to an elliptical shape of the interior chamber of the housing 112 defined by the pair of gas caps 130a, 130b.

Blood entering the oxygenator 100 through the liquid inlet 114 passes through openings the upper cap 138 to get to the gas exchange medium 136 (shown in FIG. 14). After becoming oxygenated via diffusion of oxygen flowing through the fibers of the gas exchange medium 136 into the blood, the blood passes through the lower cap 140 before exiting the oxygenator 100 through the liquid outlet 116.

With continued reference to FIG. 15, the one or more spacers 142 of the retainer 134 may be a pair of spacers 142 positioned diametrically opposite to each other. The spacers 142 may be positioned at an outer edge of the upper cap 138 and the lower cap 140 and are configured to maintain the upper cap 138 and the lower cap 140 spaced apart from each other by a predetermined distance. The spacers 142 may extend substantially parallel with the longitudinal axis 124 of the oxygenator 10 (shown in FIG. 11) and be positioned equidistantly on opposite sides of the longitudinal axis 124. The spacers 142 may be positioned at the maximum radial dimension of the elliptical shape (measured from the longitudinal axis 124) of the upper cap 138 and the lower cap 140, for example. The one or more spacers 142 may be removably or non-removably connected to the upper cap 138 and the lower cap 140. In some examples or aspects, the one or more spacers 142 may be removably connected to the upper cap 138 and monolithically formed with the lower cap 140.

The gas exchange medium 136 is disposed within the space between the upper cap 138 and the lower cap 140. The gas exchange medium 136 is configured for diffusing a gas flowing therethrough into the liquid flowing around the gas exchange medium 136. In some examples or aspects, the gas exchange medium 136 includes a plurality of subunits 152, shown in FIG. 16, that are stacked on top each other between the upper cap 138 and the lower cap 140. Each subunit 152 is made up of a plurality of layers of fiber mats, with each fiber mat having a plurality of individual hollow fibers. The fibers are configured to carry a gas, such as oxygen, in such a manner that allows the gas to be taken up by a liquid, such as blood, flowing around the fibers, and to absorb any other gas given off by the liquid, such as carbon dioxide. The gas exchange medium 136 provides the required surface area for the gas exchange to occur.

In some examples or aspects, the plurality of subunits 152 may be identical to each other in at least one characteristic, such as size, shape, thickness, number of layers of fibers mats, type of fiber mats, and orientation of layers of fiber mats relative to each other. In other examples or aspects, at least one of the plurality of subunits 152 may differ from other subunits in at least one characteristic, such as size, shape, thickness, number of layers of fibers mats, type of fiber mats, and orientation of layers of fiber mats relative to each other. For example, the number of layers of fiber mats in each subunit 152 may vary such that a thickness of the subunits 152 varies. The thickness of the subunits 152 may be varied progressively along the length of the gas exchange medium 136 between the upper cap 138 and the lower cap 140 of the retainer 34.

Figure 16:
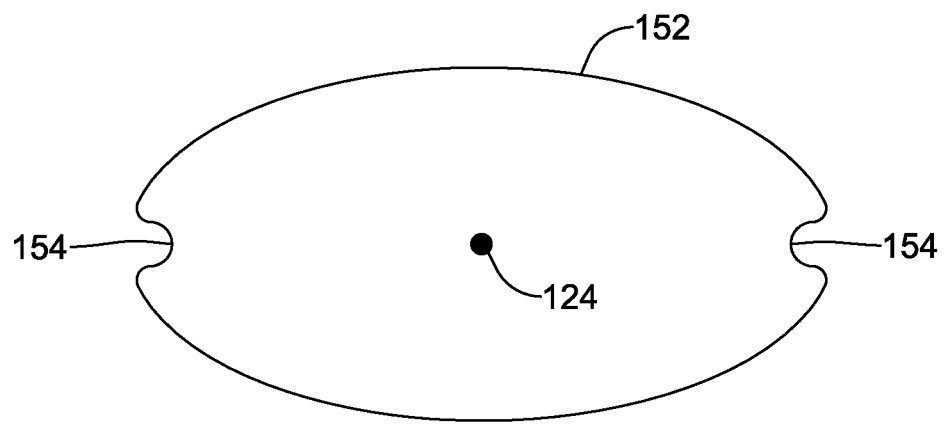
FIG. 16 is a top view of a subunit of a gas exchange medium for use with the blood oxygenator of FIG. 11.

With continued reference to FIG. 16, each subunit 152 of the gas exchange medium 136 may have a substantially elliptical shape that corresponds to the elliptical shape of the upper cap 138 and the lower cap 140 of the retainer 134. The centroid of the elliptical shape of each subunit 152 may be centered on the longitudinal axis 124 of the housing 112 when positioned within the housing 112. Each subunit 152 may have one or more notches 154 configured to receive at least a portion of the corresponding one or more spacers 142. For example, each subunit 152 may have opposing notches 154 positioned at the maximum radial dimension of the elliptical shape (measured from the longitudinal axis 124) that mate with and receive the spacers 142. In this manner, rotation of the subunits 152 about the longitudinal axis of the gas exchange medium 136 can be prevented in order to maintain a desired orientation of the hollow fibers between adjacent subunits 152.

Figure 17:
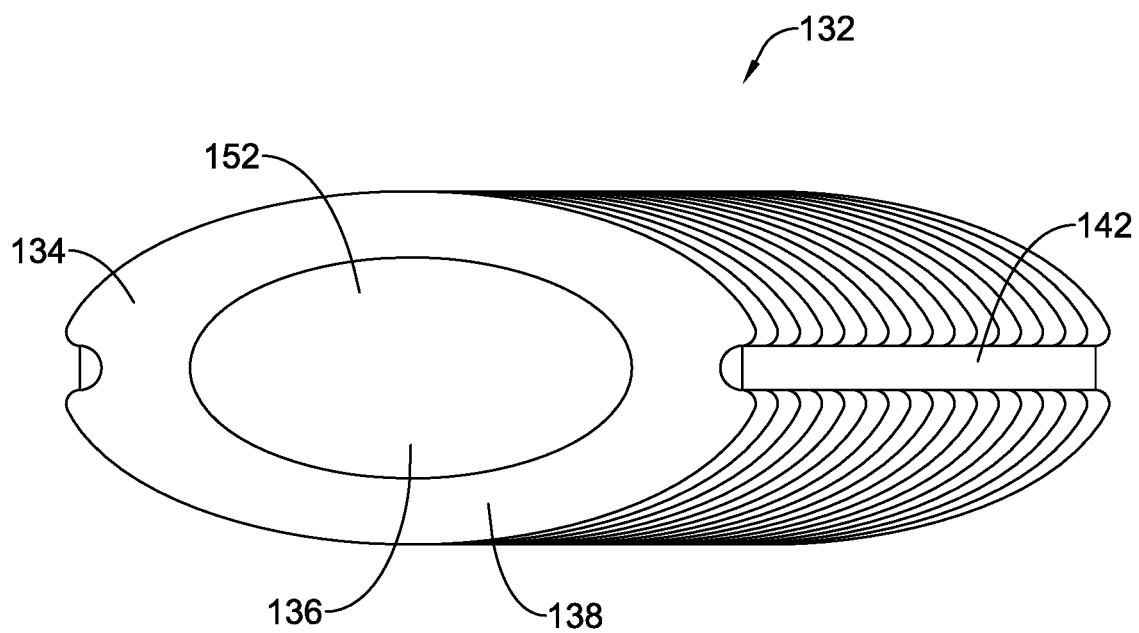
FIG. 17 is a top view of a gas exchange assembly for use with the blood oxygenator of FIG. 11.
Figure 18:
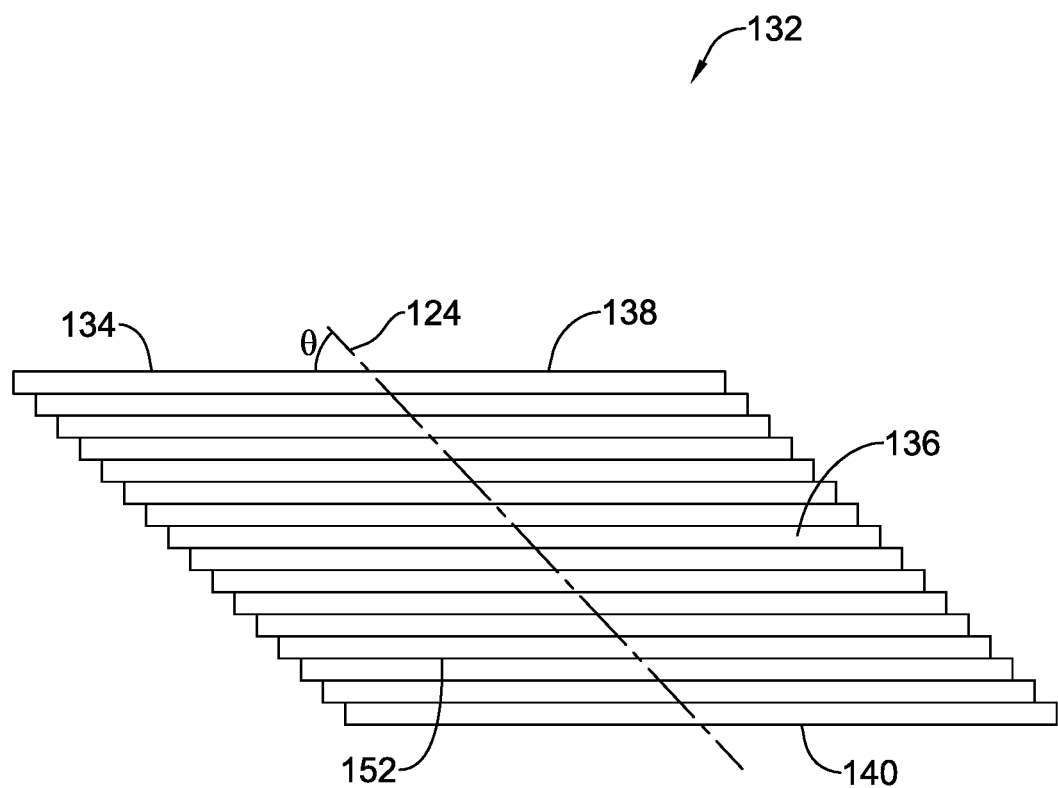
FIG. 18 is a side view of the gas exchange assembly shown in FIG. 17.

With reference to FIGS. 17 and 18, the gas exchange assembly 132 is shown separate from the oxygenator 100 and prior to being potted with a potting material. The gas exchange assembly 132 includes a retainer 134 configured to hold the gas exchange medium 136. The retainer 134 holds the gas exchange medium 136 and maintains the spacing between individual subunits of the gas exchange medium 136 prior to potting, as described herein. The retainer 134 has an upper cap 138 spaced apart from a lower cap 140 by one or more spacers 142. The upper cap 138 is shaped to be received within the interior chamber of the housing 112 such that the upper cap 138 is positioned proximate to the liquid inlet cap 126. Similarly, the lower cap 140 is shaped to be received within the interior chamber of the housing 112 such that the lower cap 140 is positioned proximate to the liquid outlet cap 128. In some examples or aspects, the upper cap 138 and the lower cap 140 have a substantially elliptical shape that corresponds to an elliptical shape of the interior chamber of the housing 112.

Figure 19:
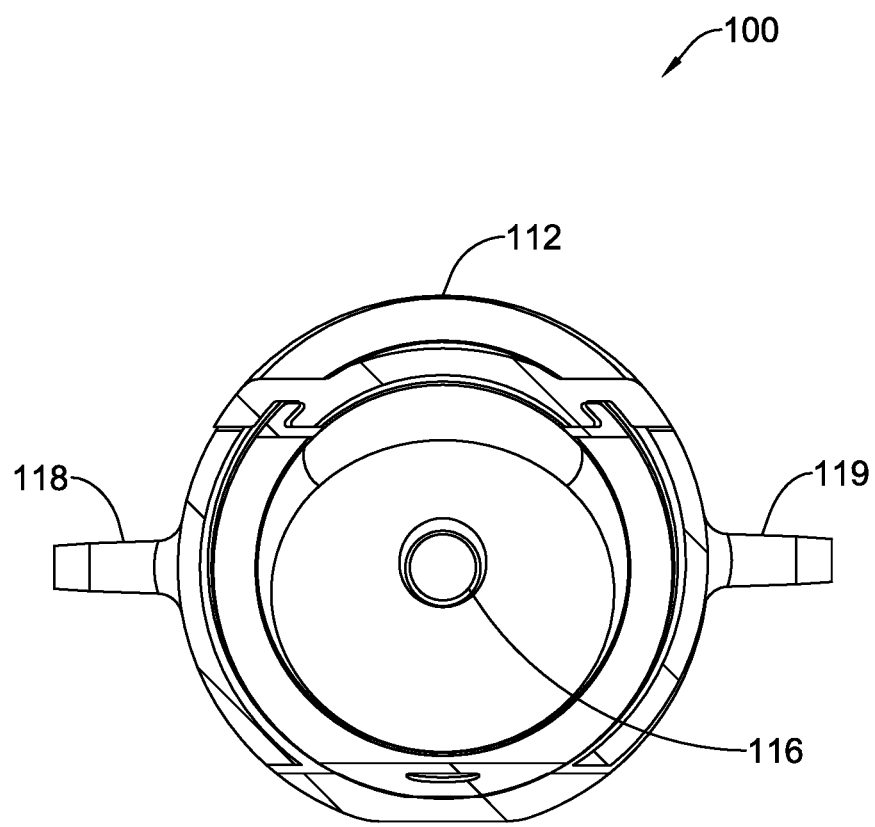
FIG. 19 is a cross-sectional view of the blood oxygenator shown in FIG. 11 taken along line 19-19.

With reference to FIG. 18, the ellipse configuration of the oxygenator 100 is achieved by stacking the individual subunits 152 that make up the gas exchange medium 136. The individual subunits 152 may lie in a plane parallel to adjacent subunits 152. Thus, the subunits 152 may be stacked such that an axis extending through the centroid of each subunit 152 is at an acute angle to a plane that the upper surface and/or lower surface of each subunit 152 lies in. The axis extending through the centroids may be coaxially or otherwise parallel to the longitudinal axis 124 of the housing 112. Accordingly, adjacent subunits 152 may be stacked with the outer periphery offset from adjacent subunits 152 and at an angle relative to one another rather than flat on top of each other as is seen in the oxygenator 10 shown in FIG. 4. Each subunit 152 is in the shape of an ellipse, and in the centroid of adjacent subunits 152 are skewed at a desired angle, such as the 30 degree angle shown in FIG. 18. Each subunit 152 is laid offset to the adjacent subunit 152 such that the stack is tilted away from the vertical axis at the desired angle. In other words, the stack of the plurality of subunits 152 forming the gas exchange medium 136 is tilted at the acute angle Θ relative to the longitudinal axis 124. This allows the cross section taken transverse to the longitudinal axis to be mostly circular (this is the cross section the blood "sees" visualizable by looking down the long axis), as shown in FIG. 19. The subunits 152 themselves are wider than the equivalent surface area circular cross section bundle which allows fewer subunits 152 to be used to get a desired surface area. This may allow for lower pressure drop as well as manufacturing and material efficiency. Angled fiber layers like this may promote mixing as well which may enhance gas exchange. This configuration allows a wider bundle without significantly altering the aspect ratio of the final device. A wider bundle device may be made without making it look like a pancake.

Figure 20:
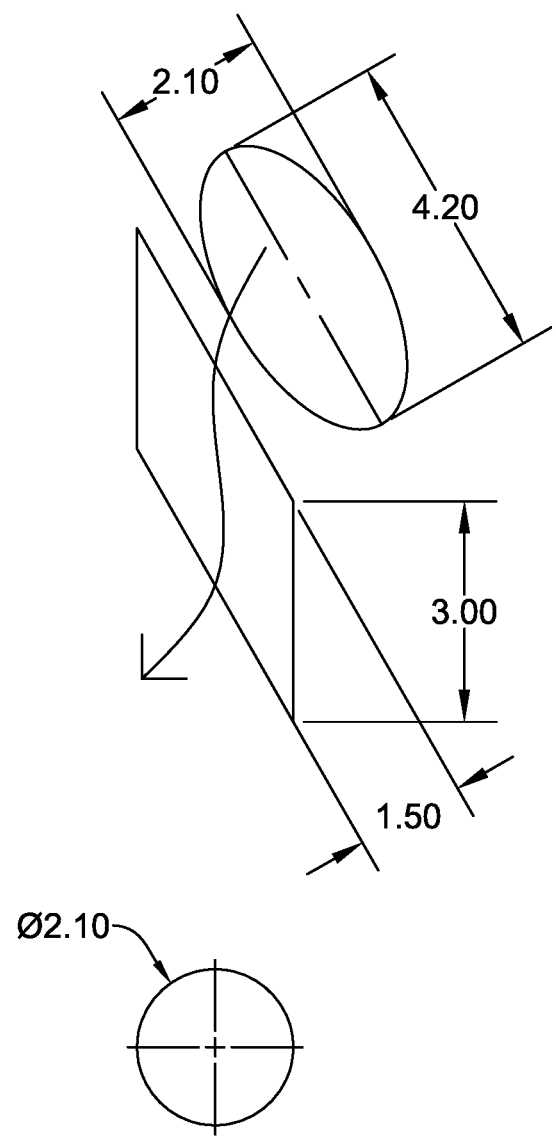
FIGS. 20-23 show various relative bundle volumes and ellipse angles for the gas exchange assembly.
Figure 21:
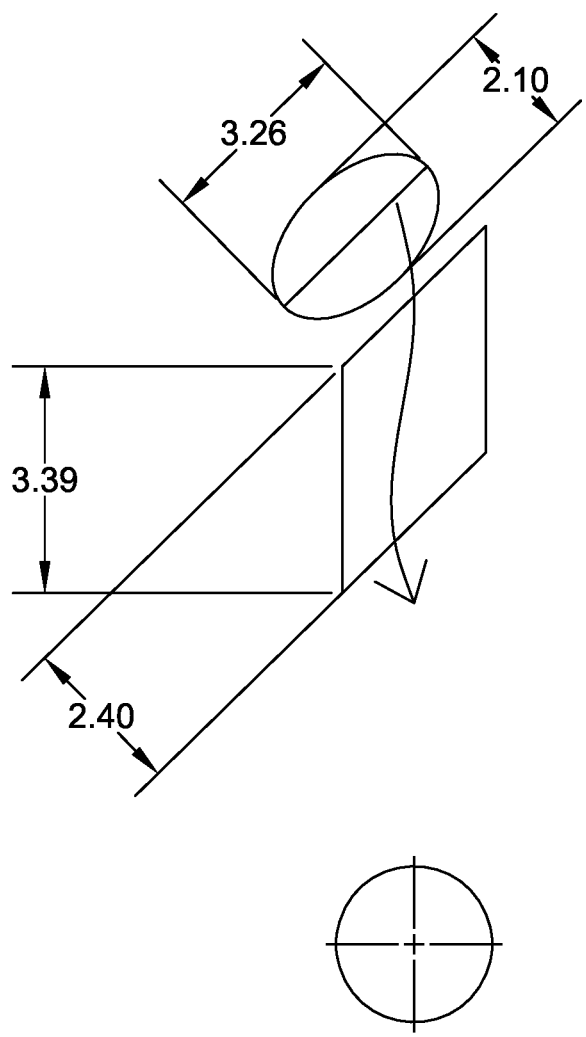
Figure 22:
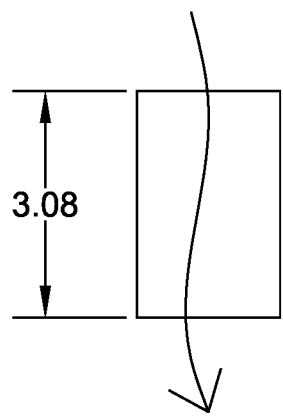
Figure 22:
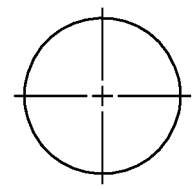
Figure 23:
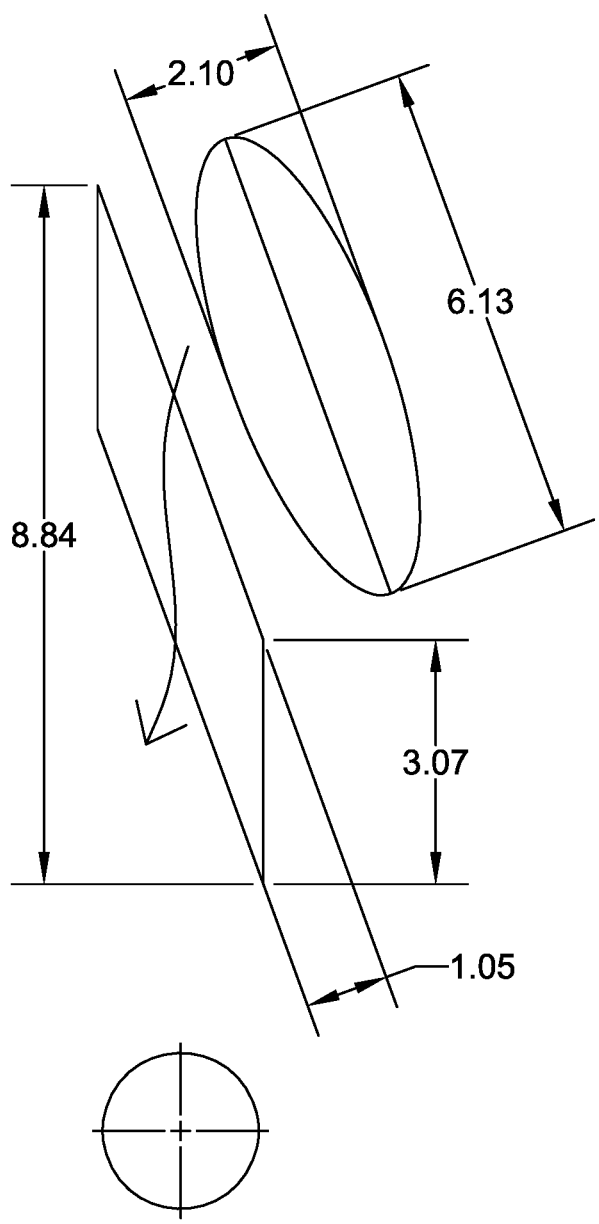

FIGS. 20-23 show various relative bundle volumes and ellipse angles needed to achieve a 1.3 square meter surface area with angled and offset subunits 52, 152 for the gas exchange assembly 32, 132. The dimensions of the subunit stacks in FIGS. 20-23 are in inches. The various assemblies have ellipse angles of 20 to 90 degrees, yet each assembly maintains a 1.3 square meter surface area. The gas exchange assembly 32 shown in FIGS. 1-6 is at an angle Θ of 90 degrees, as shown in FIG. 22, and the gas exchange assembly 132 shown in FIGS. 11-19 is at an angle Θ of 30 degrees, as shown in FIG. 20. The gas exchange assembly shown in FIG. 20 is skewed at an angle of 30 degrees and has an area ratio of 1:2, the gas exchange assembly shown in FIG. 21 is skewed at an angle of 45 degrees and has an area ratio of 1:1.41, the gas exchange assembly shown in FIG. 22 is at an angle of 90 degrees, and the gas exchange assembly shown in FIG. 23 is skewed at an angle of 20 degrees and has an area ratio of 1:2.93. A larger ellipse angle (taken relative to the vertical axis) has the advantage of allowing the bundle to be thinner, utilizing fewer subunits 52, 152, while maintaining the same surface area. For example, the gas exchange assembly 132 with an angle Θ of 30 degrees may have a thickness of 1.5 inches (FIG. 20), while the gas exchange assembly 32 with an angle Θ of 90 degrees has a thickness of 3.08 inches (FIG. 22), yet the two assemblies have the same surface area of 1.3 square meters. A thinner stack of subunits 52, 152 has the advantage of providing a shorter blood path through the stack, which lowers the amount of pressure needed to push the blood through the device.

While examples or aspects of an improved blood oxygenator are provided in the foregoing description, those skilled in the art may make modifications and alterations to these examples or aspects without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

What is claimed is:

1. A blood oxygenator comprising:
    a housing having a first end opposite a second end with a sidewall extending between the first end and the second end along a longitudinal axis, the housing defining an interior chamber having a liquid inlet at the first end and a liquid outlet at the second end; and
    a gas exchange assembly positioned within the interior chamber, the gas exchange assembly comprising:
        a retainer having an upper cap spaced apart from a lower cap by one or more spacers; and
        a gas exchange medium disposed between the upper cap and the lower cap, wherein the gas exchange medium comprises a plurality of subunits stacked on top of each other, each subunit comprising a plurality of layers of hollow fiber mats, wherein the plurality of subunits are stacked offset from one another such that an axis extending through a centroid of each of the subunits is at an acute angle relative to the longitudinal axis of the housing.

2. The blood oxygenator of claim 1, wherein the liquid inlet is formed on a liquid inlet cap enclosing the first end of the housing.

3. The blood oxygenator of claim 1, wherein the liquid outlet is formed on a liquid outlet cap enclosing the second end of the housing.

4. The blood oxygenator of claim 1, wherein the housing has a circular cross-sectional shape.

5. The blood oxygenator of claim 1, wherein the upper cap and the lower cap each have a plurality of openings.

6. The blood oxygenator of claim 1, wherein the one or more spacers is a pair of spacers positioned diametrically opposite to each other.

7. The blood oxygenator of claim 1, wherein the upper cap is removable from the one or more spacers.

8. The blood oxygenator of claim 1, wherein the plurality of subunits are identical to each other in at least one characteristic.

9. The blood oxygenator of claim 8, wherein the plurality of subunits are identical to each other in all characteristics.

10. The blood oxygenator of claim 8, wherein the at least one characteristic is a size of the subunit, a shape of the subunit, a thickness of the subunit, a number of layers of hollow fiber mats, and an angle of orientation of layers of hollow fiber mats.

11. The blood oxygenator of claim 1, wherein at least one of the plurality of subunits differs from other subunits in at least one characteristic.

12. The blood oxygenator of claim 11, wherein the at least one characteristic is a size of the subunit, a shape of the subunit, a thickness of the subunit, a number of layers of hollow fiber mats, and an angle of orientation of layers of hollow fiber mats.

13. The blood oxygenator of claim 1, wherein the plurality of subunits are elliptical in shape.

14. The blood oxygenator of claim 1, wherein the angle is between 20 degrees and 45 degrees.

15. A blood oxygenator comprising:
    a housing having a first end opposite a second end with a sidewall extending between the first end and the second end along a longitudinal axis, the housing defining an interior chamber having a liquid inlet at the first end and a liquid outlet at the second end; and
    a gas exchange assembly positioned within the interior chamber, the gas exchange assembly comprising:
        a gas exchange medium disposed within the interior chamber, wherein the gas exchange medium comprises a plurality of subunits stacked on top of each other, each subunit lying in a plane at an acute angle to the longitudinal axis, wherein the plurality of subunits are stacked offset from one another such that an axis extending through the centroid of each of the subunits is at an acute angle relative to the longitudinal axis of the housing.

16. The blood oxygenator of claim 15, wherein each subunit comprises a plurality of layers of hollow fiber mats.

17. The blood oxygenator of claim 15, wherein the interior chamber has an elliptical shape taken in a plane at an acute angle to the longitudinal axis.

18. The blood oxygenator of claim 17, wherein each of the plurality of subunits has an elliptical shape.

* * * * *